(12) United States Patent
Single

(10) Patent No.: US 10,426,409 B2
(45) Date of Patent: Oct. 1, 2019

(54) METHOD AND DEVICE FOR DETECTING A NEURAL RESPONSE IN A NEURAL MEASUREMENT

(71) Applicant: Saluda Medical Pty Ltd, Artarmon (AU)

(72) Inventor: Peter Scott Vallack Single, Artarmon (AU)

(73) Assignee: Saluda Medical Pty Ltd, Artarmon, New South Wales (AU)

( * ) Notice: Subject to any disclaimer, the term of this patent is extended or adjusted under 35 U.S.C. 154(b) by 413 days.

(21) Appl. No.: 15/037,038

(22) PCT Filed: Nov. 22, 2014

(86) PCT No.: PCT/AU2014/050369
§ 371 (c)(1),
(2) Date: May 16, 2016

(87) PCT Pub. No.: WO2015/074121
PCT Pub. Date: May 28, 2015

(65) Prior Publication Data
US 2016/0287182 A1    Oct. 6, 2016

(30) Foreign Application Priority Data
Nov. 22, 2013    (AU) .................................. 2013904519

(51) Int. Cl.
*A61B 5/00* (2006.01)
*A61N 1/36* (2006.01)
(Continued)

(52) U.S. Cl.
CPC ........ *A61B 5/7246* (2013.01); *A61B 5/04001* (2013.01); *A61B 5/6846* (2013.01);
(Continued)

(58) Field of Classification Search
CPC ..... A61B 5/04; A61B 5/04001; A61B 5/6846; A61B 5/7203; A61B 5/7246; A61N 1/36071; A61N 1/36139
See application file for complete search history.

(56) References Cited

U.S. PATENT DOCUMENTS 3,736,434 A    5/1973    Darrow
3,817,254 A    6/1974    Maurer
(Continued)

FOREIGN PATENT DOCUMENTS

EP    0219084    4/1987
EP    0998958 B1    8/2005
(Continued)

OTHER PUBLICATIONS

Brown et al., "Impact of Deep Brain Stimulation on Upper Limb Askinesia in Parkingson's Disease", Annals of Neurology, 45, No. 4, 1999, pp. 473-488.
(Continued)

*Primary Examiner* — Max F Hindenburg
(74) *Attorney, Agent, or Firm* — KPPB LLP

(57) ABSTRACT

A method for processing a neural measurement obtained in the presence of artifact, in order to detect whether a neural response is present in the neural measurement. A neural measurement is obtained from one or more sense electrodes. The neural measurement is correlated against a filter template, the filter template comprising at least three half cycles of an alternating waveform, amplitude modulated by a window. From an output of the correlating, it is determined whether a neural response is present in the neural measurement.

15 Claims, 9 Drawing Sheets

(51) Int. Cl.
  *G06K 9/00*     (2006.01)
  *A61B 5/04*     (2006.01)

(52) U.S. Cl.
  CPC .......... *A61B 5/7203* (2013.01); *A61B 5/7282* (2013.01); *A61N 1/36071* (2013.01); *A61N 1/36139* (2013.01); *G06K 9/00496* (2013.01); *A61B 2562/046* (2013.01)

(56) References Cited

U.S. PATENT DOCUMENTS

| | | |
|---|---|---|
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van et al. |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,898,582 B2 | 5/2005 | Lange et al. |
| 7,089,059 B1 | 8/2006 | Pless |
| 7,171,261 B1 | 1/2007 | Litvak et al. |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,734,340 B2 | 6/2010 | De |
| 7,742,810 B2 | 6/2010 | Moffitt |
| 7,792,584 B2 | 9/2010 | Van et al. |
| 7,818,052 B2 | 10/2010 | Litvak et al. |
| 7,831,305 B2 | 11/2010 | Gliner |
| 7,835,804 B2 | 11/2010 | Fridman et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,359,102 B2 | 1/2013 | Thacker et al. |
| 8,494,645 B2 | 7/2013 | Spitzer et al. |
| 8,588,929 B2 | 11/2013 | Davis et al. |
| 8,670,830 B2 | 3/2014 | Carlson et al. |
| 8,886,323 B2 | 11/2014 | Wu et al. |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225767 A1 | 9/2007 | Daly |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0147155 A1 | 6/2008 | Swoyer |
| 2008/0183076 A1 | 7/2008 | Witte |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2009/0033486 A1 | 2/2009 | Costantino et al. |
| 2009/0082691 A1 | 3/2009 | Denison et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |

(56) References Cited

U.S. PATENT DOCUMENTS

| | | |
|---|---|---|
| 2010/0058126 A1 | 3/2010 | Chang et al. |
| 2010/0069835 A1 | 3/2010 | Parker |
| 2010/0069996 A1 | 3/2010 | Strahl et al. |
| 2010/0070007 A1 | 3/2010 | Parker |
| 2010/0070008 A1 | 3/2010 | Parker |
| 2010/0106231 A1 | 4/2010 | Torgerson |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De et al. |
| 2011/0204811 A1 | 8/2011 | Pollmann-retsch |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0101552 A1 | 4/2012 | Lazarewicz et al. |
| 2012/0109236 A1 | 5/2012 | Jacobson et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0276195 A1 | 9/2014 | Papay et al. |
| 2014/0277250 A1 | 9/2014 | Su et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0358024 A1 | 12/2014 | Nelson et al. |
| 2015/0018699 A1 | 1/2015 | Zeng et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0166164 A1 | 6/2016 | Obradovic et al. |
| 2016/0287126 A1 | 10/2016 | Parker et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0216587 A1 | 8/2017 | Parker |
| 2017/0361101 A1 | 12/2017 | Single |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |

FOREIGN PATENT DOCUMENTS

| | | |
|---|---|---|
| EP | 2019716 A | 11/2007 |
| EP | 2243510 A2 | 10/2010 |
| EP | 2443995 A2 | 4/2012 |
| EP | 2707095 A1 | 3/2014 |
| JP | 2013527784 A | 7/2013 |
| WO | 1983003191 A | 9/1983 |
| WO | 1993001863 A1 | 2/1993 |
| WO | 9612383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 20040103455 | 12/2004 |
| WO | 2005032656 A1 | 4/2005 |
| WO | 2005105202 A1 | 11/2005 |
| WO | 2006091636 A2 | 8/2006 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 20160011512 | 1/2016 |

(56) References Cited

FOREIGN PATENT DOCUMENTS

| WO | 2016077882 A1 | 5/2016 |
|---|---|---|
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016191807 A1 | 12/2016 |
| WO | 2016191808 A1 | 12/2016 |
| WO | 2016191815 A1 | 12/2016 |
| WO | 2017173493 A1 | 10/2017 |
| WO | 2017219096 A1 | 12/2017 |

OTHER PUBLICATIONS

Budagavi et al., "Modelling of compound nerve action potentials health and disease", Engineering in Medicine and Biology Society, 1992 14th Annual International Conference of the IEEE. vol. 6. IEEE, 1992. pp. 2600-2601.

Coquery et al., "Backward and forward masking in the perception of cutaneous stimuli", Perception & Psychophysics, 1973, vol. 13.No. 2, pp. 161-163.

Dawson, G. D. "The relative excitability and conduction velocity of sensory and motor nerve fibres in man", Journal of Physiology, 1956, vol. 131(2), pp. 436-451.

Devergnas et al., A "Cortical potentials evoked by deep brain stimulation in the subthalamic area", Front Syst Neurosci. 2011; 5: 30. May 13, 2011. doi:10.3389/fnsys.2011.00030.

Dijkstra, E. A. "Ultrasonic Distance Detection for a Closed-Loop Spinal Cord Stimulation System", Proceedings—19th International Conference—IEEE/EMBS Oct. 30-Nov. 2, 1997, Chicago, IL. 4 pgs.

Dillier, N et al., "Measurement of the electrically evoked compound action potential via a neural response telemetry system", Ann. Otol. Rhinol. Laryngol, vol. 111, No. 5, May 2002, pp. 407-414.

Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10. 1152/jn.00729.2002.

England et al., "Increased Numbers of Sodium Channels Form Along Demyelinated Axons", Brain Research 548, No. 1-2 (May 10, 1991): 334-337.

Fagius, J. et al. "Sympathetic Reflex Latencies and Conduction Velocities in Normal Man", Journal of Neurological Sciences, 1980. vol. 47, pp. 433-448.

Falowski et al., "Spinal Cord Stimulation: an update", Neurotherapeutics: The Journal of the American Society for Experimental NeuroTherapeutics 5, No. 1, Jan. 2008, pp. 86-99.

Fuentes et al., "Spinal Cord Stimulation Restores Locomotion in Animal Models of Parkinson's Disease", Science, vol. 323, No. 5921, Mar. 20, 2009, pp. 1578-1582.

George et al., "Vagus nerve stimulation: a new tool for brain research and therapy", Biological Psychiatry 47, No. 4, Feb. 15, 2000, pp. 287-295.

Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.

Gorman et al., "ECAP Mapping of the Spinal Cord: Influence of Electrode Position on Aβ Recruitment", (2012), in 16th Annual Meeting. Presented at the North American Neuromodulation Society, Las Vegas, NV.

Gorman et al., "Neural Recordings for Feedback Control of Spinal Cord Stimulation: Reduction of Paresthesia Variability", 2013,In International Neuromodulation Society 11th World Congress. Presented at the International Neuromodulation Society 11th World Congress, Berlin, Germany.

Hallstrom et al, "Distribution of lumbar spinal evoked potentials and their correlation with stimulation-induced paresthesiae", (1991), Electroencephalography and clinical neurophysiology 80:126-139.

Harper, A. A. et al., "Conduction Velocity is Related to Morphological Cell Type in Rat Dorsal Root Ganglion Neurones", J. Physiol, (1985), 359, pp. 31-46.

Holsheimer et al., "Optimum Electrode Geometry for Spinal Cord Stimulation: the Narrow Bipole and Tripole", Medical and Biological Engineering and Computing, 35, No. 5, 1997, pp. 493-497.

Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.

Hui, Ouyang et al., "Compression Induces Acute Demyelination and Potassium Channel Exposure in Spinal Cord", Journal of Neurotrauma 27, No. 6, Jun. 2010, 1109-1120, doi:10.1089/neu. 2010.1271.

Kent et al., "Instrumentation to Record Evoked Potentials for Closed-Loop Control of Deep Brain Stimulation", Conf. Proc. IEEE Eng. Med Biol. Sol, Aug. 2012, 10 pgs.

Kent et al., AR, "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.

Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/50306-4522(98)00022-0.

Krames et al., "Neuromodulation", 1st Edition, Academic Press, 2009, p. 540-541.

Krarup, Christian, "Compound sensory action potential in normal and pathological human nerves", Muscle & nerve, vol. 29, No. 4 (2004), pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, 53, No. 4, 1999, pp. 871-874.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott, "The Electrode-Tissue Interface During Recording and Stimulation in the Central Nervous System", published on May 2010.

Levy et al., "Incidence and Avoidance of Neurologic Complications with Paddle Type Spinal Cord Stimulation Leads", Neuromodulation 14(15), Sep. 2011, pp. 412-422.

Li et al., S, "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/ jn.00855.2002.

Macefield, "Spontaneous and Evoked Ectopic Discharges Recorded from Single Human Axons", Muscle & Nerve 21, No. 4, Apr. 1998, pp. 461-468.

Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.

Markandey, Vishal, "ECG Implementation on the TMS320C5515 DSP Medical Development Kit (MDK)", Texas Instruments Application Report Jun. 2010, 35 pgs.

(56) References Cited

OTHER PUBLICATIONS

Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
Matzner et al., "Na+ Conductance and the Threshold for Repetitive Neuronal Firing", Brain Research 597, No. 1 (Nov. 27, 1992): 92-98, doi:10.1016/0006-8993(92)91509-D.
Mcgill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445 1982.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, 567-578.
Parker et al., "Closing the Loop in Neuromodulation Therapies: Spinal Cord Evoked Compound Action Potentials During Stimulation for Pain Management (230)", 2011, In 15th Annual Meeting, North American Neuromodulation Society (p. 48). Presented at the North American Neuromodulation Society, Las Vegas.
Parker et al., "Compound action potentials recorded in the human spinal cord during neurostimulation for pain relief", Pain, 2012, vol. 153, pp. 593-601.
Parker et al., "Electrically Evoked Compound Action Potentials Recorded From the Sheep Spinal Cord", Neuromodulation, vol. 16, 2013, pp. 295-303.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
Extended European Search Report for EP Application 12785483.4 completed Sep 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 9 pgs.
Extended European Search Report for European Application No. 14861553.7, Search completed Jun. 8 2017, dated Jun. 19, 2017, 8 pgs.
Extended European Search Report for European Application No. 14863597.2, Search completed Jun. 6, 2017, dated Jun. 13, 2017, 9 pgs.
Extended European Search Report for European Application No. 13853514.1, Search completed Jun. 8, 2016, dated Jun. 15, 2016, 07 pgs.
International Preliminary Report on Patentability for International Application No. PCT/AU2012/001441, Report dated May 27, 2014, 10 pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2015/050135, Search completed Jun. 30, 2015, dated Jun. 30, 2015, 26 pgs.
International Search Report and Written Opinion for International Application No. PCT/AU2015/050422, Search completed Oct. 14, 2015, dated Oct. 14, 2015, 17 pgs.
International Search Report and Written Opinion for International Application No. PCT/AU2015/050724, Search completed May 9, 2016, dated May 9, 2016, 8 pgs.
International Search Report and Written Opinion for International Application No. PCT/AU2015/050753, Search completed Feb. 10, 2016, dated Feb. 10, 2016, 10 pgs.
International Search Report and Written Opinion for International Application No. PCT/AU2015/050787, Search completed Mar. 16, 2016, dated Mar. 16, 2016, 10 pgs.
International Search Report and Written Opinion for International Application No. PCT/AU2016/050019, Search completed May 4, 2016, dated May 4, 2016, 16 pgs.
International Search Report and Written Opinion for International Application No. PCT/AU2015/050215, Search completed Jul. 30, 2015, dated Jul. 30, 2015, 8 pgs.
International Search Report for Australian Application 2011901829 Search Completed Feb. 6, 2012, dated Feb. 7, 2012, 3 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.

(56) References Cited

OTHER PUBLICATIONS

Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wkipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
International Search Report & Written Opinion for International Application No. PCT/AU2013/001280, Search Completed Jan. 16, 2014, dated Jan. 16, 2014, 8 pgs.
International Search Report & Written Opinion for International Application PCT/AU2013/001279, Search Completed Jan. 9, 2014, dated Jan. 9, 2014, 9 pgs.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Andreassen, S. et al. "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R. "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.

Extended European Search Report for European Application No. 16739680.3, Search completed Jun. 1, 2018, dated Jun. 12, 2018, 9 Pgs.
European Search Report for European Application No. 15861444.6, Search.completed Jul. 13, 2018, dated Jul. 23, 2018, 8 pgs.
French et al., "Information transmission at 500 bits/s by action potentials in a mechanosensory neuron of the cockroach", Neuroscience Letters, vol. 243, No. 1-3, Feb. 1, 1998, pp. 113-116.
Herreras, "Local Field Potentials: Myths and Misunderstandings", Frontiers in Neural Circuits, Dec. 15, 2016, vol. 10, Article 1101, 16 pgs
International Search Report and Written Opinion for International Application No PCT/AU2014/050369, Search completed Feb. 20, 2015, dated Feb. 20, 2015, 14 Pgs.
Franke, Felix et al., "An Online Spike Detection and Spike Classification Algorithm Capable of Instantaneous Resolution of Overlapping Spikes", Journal of Computational Neuroscience, 2010, vol. 29, No. 1-2, pp. 127-148.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Roy, S. H. et al., "Effects of Electrode Location on Myoelectric Conduction Velocity and Median Frequency Estimates", J. Appl. Physiol. 61 (4), 1986, pp. 1510-1517.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.

(56) References Cited

OTHER PUBLICATIONS

Villavicencio, Alan T., "Laminectomy versus Percutaneous Electrode Placement for Spinal Cord Stimulation," Neurosurgery, vol. 46 (2), Feb. 2000, pp. 399-405.
Vleggeert et al., Lankamp, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi: 10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
International Preliminary Report on Patentability for International Application No. PCT/AU2015/050753, Report dated Jun. 13, 2017, 7 pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", The Scientific World Journal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Type Search Report for International Application No. AU 2015902393, Search completed May 16, 2016, dated May 16, 2016, 8 Pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Extended European Search Report for European Application No. 15768956.3, Search completed Oct. 3, 2017, dated Oct. 10, 2017, 8 Pgs.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.

(56) References Cited

OTHER PUBLICATIONS

International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Search Report and Written Opinion for International Application No. PCT/AU2017/050296, Search completed Jul. 28, 2017, dated Jul. 28, 2017, 10 Pgs.
International Search Report and Written Opinion for International Application No. PCT/AU2017/050647, Search completed Sep. 29, 2017, dated Sep. 29, 2017, 13 Pgs.
Partial European Search Report for European Application No. 16775966.1, Search completed Oct. 26, 2018, dated Nov. 6, 2018, 11 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
He et al., "Perception threshold and electrode position for spinal cord stimulation", Pain, 59 (1994) 55-63 pages.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 Pages.
Jeffrey et al., "A reliable method for intracranial electrode implantation and chronic electrical stimulation in the mouse brain", BMC Neuroscience. Biomed Central. London. GB. vol. 14. No. 1. Aug. 6, 2013 (Aug. 6, 2013) • p. 82.
Olin et al., "Postural Changes in Spinal Cord Stimulation Perceptual Thresholds", Neuromodulation, vol. 1, No. 4, 1998, pp. 171-175.
Rattay, "Analysis of Models for External Stimulation of Axons", IEEE Transactions on Biomedical Engineering, vol. BME-33, No. 10, Oct. 1986, pp. 974-977.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Struijk, "The Extracellular Potential of a Myelinated Nerve Fiber in an Unbounded Medium and in Nerve Cuff Models", Biophysical Journal vol. 72 Jun. 1997 2457-2469.
Tronnier et al., "Magnetic Resonance Imaging with Implanted Neurostimulators: An In Vitro and In Vlvo Study", Jan. 1999, Neurosurgery, vol. 44(1), p. 118-125 (Year: 1999).

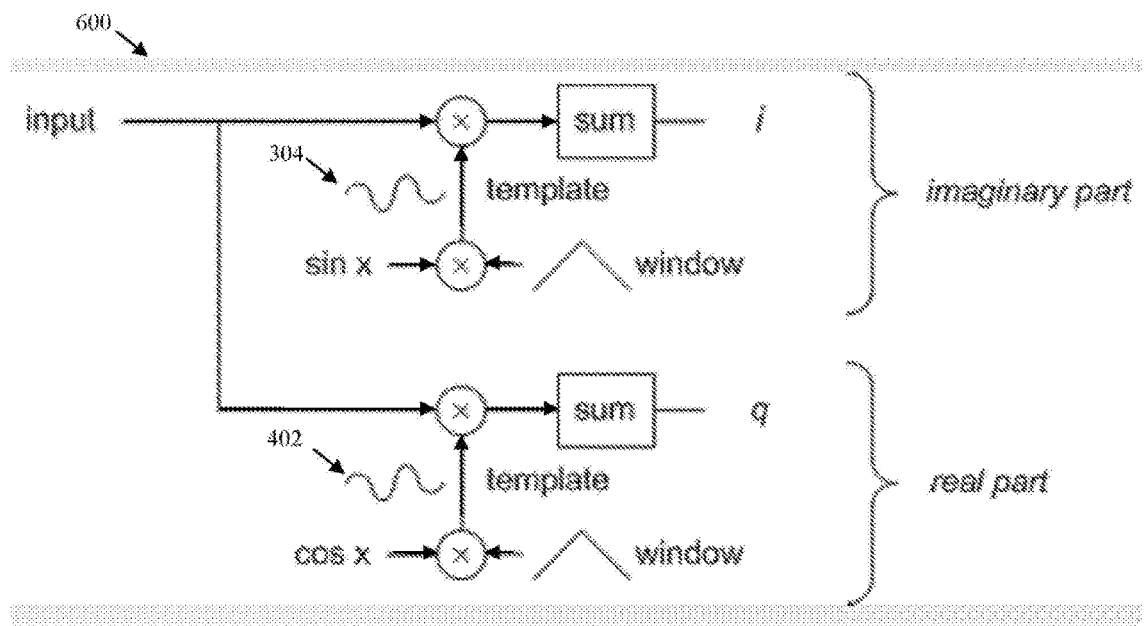
Figure 6
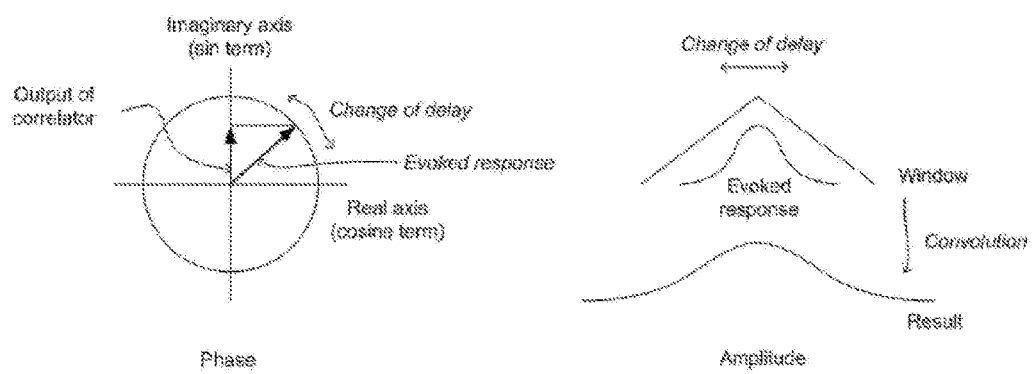
Figure 7aFigure 7b

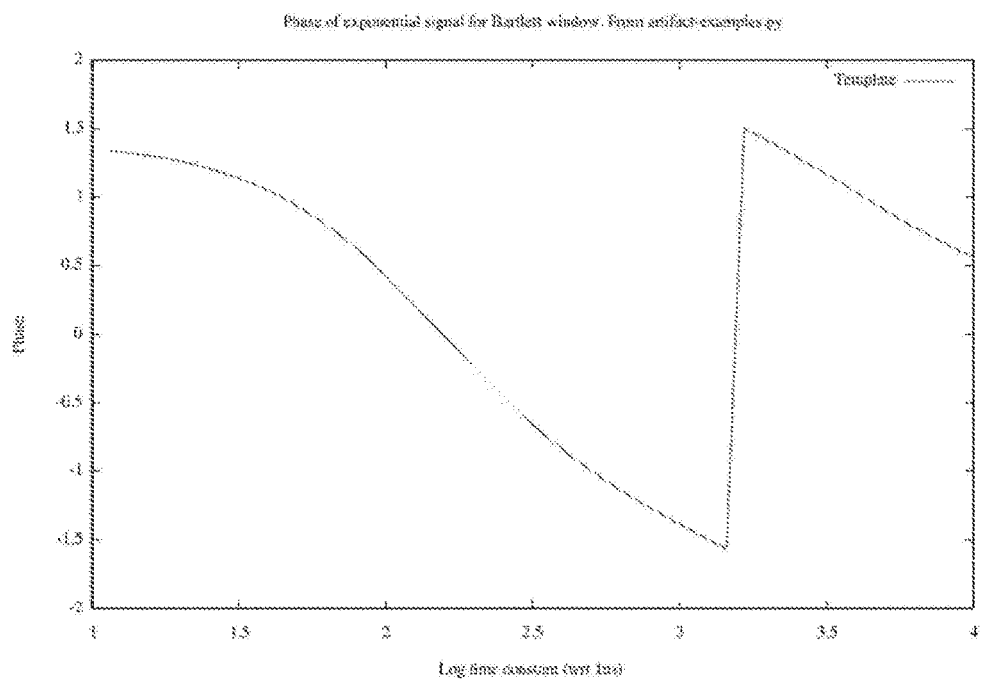
Figure 8
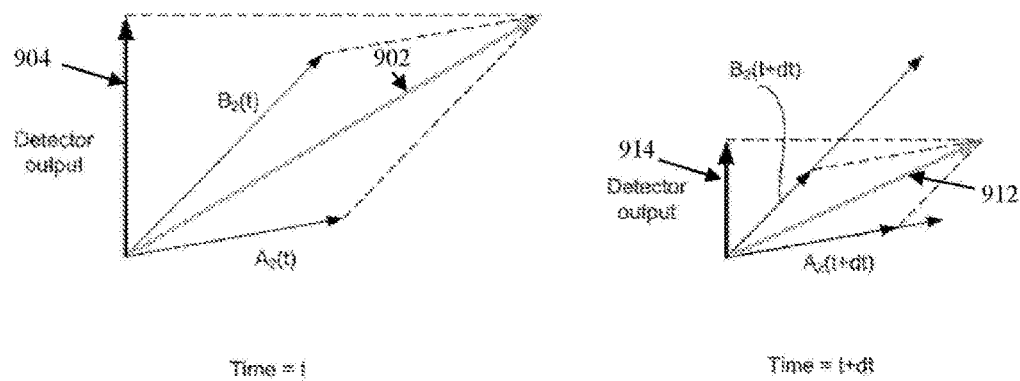
Figure 9a  Figure 9b
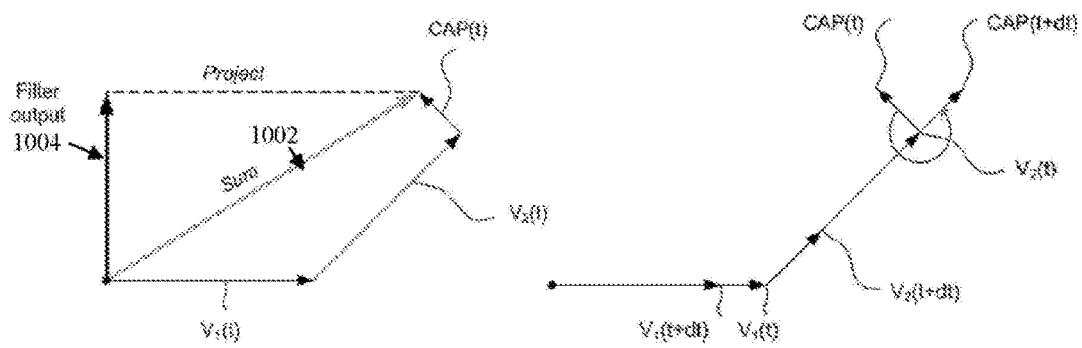
Figure 10a  Figure 10b

METHOD AND DEVICE FOR DETECTING A NEURAL RESPONSE IN A NEURAL MEASUREMENT

CROSS-REFERENCE TO RELATED APPLICATIONS

This application is a national stage of Application No. PCT/AU2014/050369 filed Nov. 22, 2014, which application claims the benefit of Australian Provisional Patent Application No. 2013904519 filed Nov. 22, 2013, the disclosures of which are incorporated herein by reference in their entirety.

TECHNICAL FIELD

The present invention relates to detection of a neural response, such as a neural response caused by a stimulus. In particular the present invention relates to detection of a compound action potential by using one or more electrodes implanted proximal to the neural pathway to obtain a neural measurement.

BACKGROUND OF THE INVENTION

Electrical neuromodulation is used or envisaged for use to treat a variety of disorders including chronic pain, Parkinson's disease, and migraine, and to restore function such as hearing and motor function. A neuromodulation system applies an electrical pulse to neural tissue in order to generate a therapeutic effect. Such a system typically comprises an implanted electrical pulse generator, and a power source such as a battery that may be rechargeable by transcutaneous inductive transfer. An electrode array is connected to the pulse generator, and is positioned close to the neural pathway(s) of interest. An electrical pulse applied to the neural pathway by an electrode causes the depolarisation of neurons, which generates propagating action potentials whether antidromic, orthodromic, or both, to achieve the therapeutic effect.

When used to relieve chronic pain for example, the electrical pulse is applied to the dorsal column (DC) of the spinal cord and the electrode array is positioned in the dorsal epidural space. The dorsal column fibres being stimulated in this way inhibit the transmission of pain front that segment in the spinal cord to the brain.

In general, the electrical stimulus generated in a neuromodulation system triggers a neural action potential which then has either an inhibitory or excitatory effect. Inhibitory effects can be used to modulate an undesired process such as the transmission of pain, or excitatory effects can be used to cause a desired effect such as the contraction of a muscle or stimulation of the auditory nerve.

The action potentials generated among a large number of fibres sum to form a compound action potential (CAP). The CAP is the sum of responses from a large number of single fibre action potentials. When a CAP is electrically recorded, the measurement comprises the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak $P_1$ in the recorded potential, then a negative peak $N_1$, followed by a second positive peak $P_2$. This is caused by the region of activation passing the recording electrode as the action potentials propagate along the individual fibres, producing the typical three-peaked response profile. Depending on stimulus polarity and the sense electrode configuration, the measured profile of some CAPs may be of reversed polarity, with two negative peaks and one positive peak.

Approaches proposed for obtaining a neural measurement are described by the present applicant in International Patent Publication No. WO 2012/155183, the content of which is incorporated herein by reference, and also by King (U.S. Pat. No. 5,913,882), Nygard (U.S. Pat. No. 5,758,651) and Daly (U.S. Patent Application No. 2007/0225767), for example.

To better understand the effects of neuromodulation and/or other neural stimuli, and for example to provide a stimulator controlled by neural response feedback, it is desirable to accurately detect a CAP resulting from the stimulus. Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, a response measurement can be more easily obtained. This is the case in surgical monitoring where there are large distances (e.g. more than 12 cm for nerves conducting at 60 ms$^{-1}$) between the stimulating and recording electrodes so that the propagation time from the stimulus site to the recording electrodes exceeds 2 ms.

However to characterize the responses from the dorsal columns, high stimulation currents and close proximity between electrodes are required, and therefore in such situations the measurement process must overcome artifact directly. However, this can be a difficult task as an observed CAP signal component in the neural measurement will typically have a maximum amplitude in the range of microvolts. In contrast a stimulus applied to evoke the CAP is typically several volts and results in electrode artifact, which manifests in the neural measurement as a decaying output of several millivolts partly or wholly contemporaneously with the CAP signal, presenting a significant obstacle to isolating or even detecting the much smaller CAP signal of interest.

For example, to resolve a 10 µV CAP with 1 µV resolution in the presence of an input 5V stimulus, for example, requires an amplifier with a dynamic range of 134 dB, which is impractical in implant systems. As the neural response can be contemporaneous with the stimulus and/or the stimulus artifact, CAP measurements present a difficult challenge of measurement amplifier design. In practice, many non-ideal aspects of a circuit lead to artifact, and as these mostly have a decaying exponential appearance that can be of positive or negative polarity, their identification and elimination can be laborious.

The difficulty of this problem is further exacerbated when attempting to implement CAP detection in an implanted device. Typical implants have a power budget which permits a limited number, for example in the hundreds or low thousands, of processor instructions per stimulus, in order to maintain a desired battery lifetime. Accordingly, if a CAP detector for an implanted device is to be used regularly (e.g. once a second), then the detector should preferably consume only a small fraction of the power budget and thus desirably should require only in the tens of processor instructions in order to complete its task.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method for processing; a neural measurement obtained in the presence of artifact, in order to detect whether a neural response is present in the neural measurement, the method comprising:

obtaining a neural measurement from one or more sense electrodes;

correlating the neural measurement against a filter template, the filter template comprising at least three half cycles of an alternating waveform, amplitude modulated by a window; and determining from an output of the correlating whether a neural response is present in the neural measurement.

According to a second aspect the present invention provides an implantable device for processing a neural measurement obtained in the presence of artifact, in order to detect whether a neural response is present in the neural measurement, the device comprising:

measurement circuitry for obtaining a neural measurement from one or more sense electrodes: and a processor configured to correlate the neural measurement against a filter template, the filter template comprising at least three half cycles of an alternating waveform, amplitude modulated by a window; and the processor further configured to determine from an output of the correlating whether a neural response is present in the neural measurement.

The window may comprise a triangular window. The triangular window may be a standard triangular window of length L comprising coefficients w(n) as follows:

For $L$ odd:
$w(n) = 2n/(L+1)$ for $1 \le n \le (L+1)/2$
$= 2 - 2n(L+1)$ for $(L+1)/2 + 1 \le n \le L$ For $L$ even:
$w(n) = (2n-1)/L$ for $1 \le n \le L/2$
$= 2 - (2n-1)/L$ for $L/2 + 1 \le n \le L$.

More preferably, the triangular window is a Bartlett window in which samples 1 and L are zero, and it is to be appreciated that the phrase triangular window herein is intended to encompass both a standard triangular window and a Bartlett window, as described above, as well as other substantially triangular or tent-shaped window functions. Alternatively, the window may comprise a Bartlett window, a Harming window, a rectangular window or a Kaiser-Bessel window of suitable beta value.

In preferred embodiments of the invention, the filter template comprises four half-cycles of an alternating waveform. Such embodiments recognise that a matched filter, comprising a three-peaked template shaped somewhat like the expected three-peaked CAP response, used to correlate against an obtained neural measurement, can optimise SNR when the noise is white, but that artifact is not white noise and that such three-peaked matched filters may perform less optimally in CAP detection in the presence of artifact.

The filter template may comprise four half cycles of a sine wave, modified by being amplitude modulated by a triangular window, thus comprising four alternating peaks. Alternatively the filter template may comprise four half cycles of a cosine wave, modified by having an amplitude fitted within a triangular window, thus comprising five alternating peaks. Inverses of such filter templates, i.e. having opposite polarity, may be employed in some embodiments. The alternating waveform in alternative embodiments may be non-sinusoidal, but is preferably a continuous curve, and may in some embodiments resemble the profile of a neural response albeit comprising four half cycles.

The present invention thus provides for selection of a filter template having improved artifact rejection. The present invention recognises that artifact can be reasonably accurately modelled as a sum of two exponentials having distinct time constants, and that because a Bartlett filter template window rejects the first three terms of a Taylor expansion of $e^x$, namely the DC, linear, and quadratic terms, such embodiments of the present invention thus facilitate artifact rejection.

According to a third aspect the present invention provides a method for processing a neural measurement obtained in the presence of artifact, in order to detect whether a neural response is present in the neural measurement, the method comprising:

obtaining a neural measurement from one or more sense electrodes;

at a first time offset, correlating the neural measurement against a first filter template to produce a first measure $m_1$, the first filter template comprising an alternating waveform of a first phase;

at the first time offset, correlating the neural measurement against a second filter template to produce a second measure $m_2$, the second filter template comprising an alternating waveform of a second phase 90 degrees offset to the first phase;

at a second time offset, being at a non-integer multiple of 180 degrees offset from the first time offset, correlating the neural measurement against the first filter template to produce a third measure $m_3$;

at the second time offset, correlating the neural measurement against the second filter template to produce a fourth measure $m_4$; and processing $m_1$ to $m_4$ to detect whether a neural response exists in the neural measurement.

According to a fourth aspect the present invention provides a device for processing a neural measurement obtained in the presence of artifact, in order to detect whether a neural response is present in the neural measurement, the device comprising:

measurement circuitry for obtaining a neural measurement from one or more sense electrodes, and a processor configured to:
at a first time offset, correlate the neural measurement against a first filter template to produce a first measure $m_1$, the first filter template comprising an alternating waveform of a first phase;

at the first time offset, correlate the neural measurement against a second filter template to produce a second measure $m_2$, the second filter template comprising an alternating waveform of a second phase 90 degrees offset to the first phase;

at a second time offset, being at a non-integer multiple of 180 degrees offset from the first time offset, correlate the neural measurement against the first filter template to produce a third measure $m_3$;

at the second time offset, correlate the neural measurement against the second filter template to produce a fourth measure $m_4$; and process $m_1$ to $m_4$ to detect whether a neural response exists in the neural measurement.

In some embodiments of the third and fourth aspects the first filter template may be anti-symmetric so as to create an imaginary DFT output, while the second filter template may be symmetric so as to create a real DFT output.

In some embodiments of the third and fourth aspects the second time offset is offset by 90 degrees, or 270 degrees, from the first time offset.

In some embodiments of the third and fourth aspects the first and/or second filter template may each comprise four half cycles of an alternating waveform, amplitude modulated by a triangular window. For example the first filter template may comprise four half cycles of a sinusoid waveform amplitude modulated by a triangular window, and the second filter template may comprise four half cycles of a cosine waveform amplitude modulated by the triangular window. Alternatively, the alternating waveform of the first and second filter templates in some embodiments of the third and fourth aspects of the invention may be amplitude modulated by a Kaiser Bessel window, for example having $\beta=6$.

The first though fourth aspects of the present invention are further advantageous when applied in relation to an implanted device, in that performing a correlation of a filter template with a neural measurement typically requires only in the tens of processor instructions, and thus consumes a suitably small fraction of the power budget of a typical implant, as compared for example to a double exponential matched filter approach which would require hundreds of processor instructions. In preferred embodiments of the first though fourth aspects of the present invention only a single point of the correlation is calculated, at a predefined optimal time delay.

Some embodiments of the first through fourth aspects of the invention may provide a method for efficiently determining an optimum time delay when a signal to artifact ratio is greater than one, at which a first or single point of the cross-correlation between the neural measurement and the filter template should be produced, the method comprising:

at an approximate time delay between the neural response and the filter template, computing real and imaginary parts of the fundamental frequency of the MT of the neural measurement;

calculating a phase defined by the real and imaginary parts;

relative to the fundamental frequency, calculating the time adjustment needed to change the calculated phase to pi/2; and defining the optimum time delay as being the sum of the approximate time delay and the time adjustment.

Other embodiments of the third and fourth aspects of the invention may provide a method for efficiently determining an optimum time delay at which a first or single point of the cross-correlation between the neural measurement and the filter template should be produced, the method comprising:

at the first time offset, correlating the neural measurement against a third filter template to produce a fifth measure $m_5$, the third filter template comprising an alternating waveform at double the frequency of the first filter template and of a third phase;

at the second time offset, correlating the neural measurement against the third filter template to produce a sixth measure $m_6$; and determining from $m_5$; and $m_6$ a decay in artifact between the first time offset and the second time offset.

The optimum time delay may then be used to define the single point at which the cross-correlation between the neural measurement and the filter template should be produced. The optimum time delay may be calculated regularly, for example prior to every attempted detection of a neural response, or occasionally, for example at one second intervals or in response to a detected change in the user's posture.

The fundamental frequency may be the frequency of the three phases of the CAP and/or may be the frequency of the four cycles of the filter template.

A length of the filter template is preferably selected so that the filter template comprises a number of filter points which, at a sampling rate at which the neural measurement is assessed, is four-thirds of the duration of a typical neural response.

In preferred embodiments the measurement is obtained in accordance with the teachings of International Patent Publication No. WO 2012/155183, by the present applicant. In further preferred embodiments the detector output is used in a closed loop feedback circuit to control neuromodulation, for example in conjunction with the techniques of International Patent Publication No. WO 2012/155188, by the present applicant, the content of which is incorporated herein by reference.

The present invention thus recognises that the amplitude of an evoked response can be measured by calculating the dot product of a neural measurement and a filter template, provided that the filter template is substantially orthogonal with the artifact and has a dot-product with the response which is close to that of a matched filter matched to the evoked response. The filter template preferably rejects DC, rejects first order signals (signals having a constant slope), and rejects low frequency signals which decay exponentially or similarly, such as artifact. The filter is preferably configured so as to be able to operate upon signals which occurred immediately after a stimulus.

While four lobes provides the optimal trade-off between rejection of artifact and noise gain, alternative embodiments of the present invention may usefully employ a filter template comprising greater or fewer lobes. In such embodiments the filter template may comprise one or more basis functions derived from a sinusoidal binomial transform (SBT), for example. In embodiments comprising a three or five lobed filter template the window preferably comprises a flat central portion, as returned by the SBT, rather than a triangular peak for example, in order to better reject DC and ramp components of a Taylor expansion and thus better reject artifact. Some embodiments of the invention may use multiple identical filter template elements, but shifted in time. Even though these are not orthogonal, a successive approximation method creating a compound template may provide better approximation. Additionally or alternatively, some embodiments may use templates that are a sum of templates of different frequencies, templates of different offset and/or templates of different numbers of lobes.

BRIEF DESCRIPTION OF THE DRAWINGS

An example of the invention will now be described with reference to the accompanying drawings, in which:

FIG. 3b illustrates a modified version of the embodiment of FIG. 3a;

FIG. 6 illustrates hardware to compute a complex term of the windowed DFT;

FIG. 7 illustrates the effect of a clinical fitting procedure of the evoked response detector;

FIG. 8 illustrates the dependency of the phase of the DFT terms of an exponential on the time constant of the exponential;

FIGS. 9a and 9b illustrate, at respective times, the detector output vector components arising from artifact only, when modelled as two exponentials;

FIGS. 10a and 10b illustrate, at respective times, the detector output vector components arising from artifact modelled as two exponentials and from an evoked response;

DESCRIPTION OF THE PREFERRED EMBODIMENTS

Figure 1:
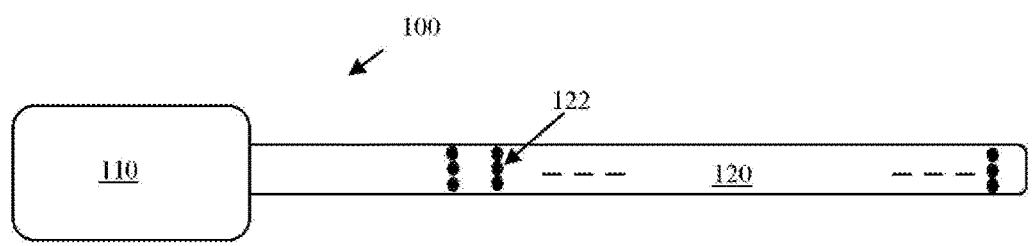
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. The control unit 110 includes a storage memory (or other storage device(s), not shown) for storing a lookup table that contains data defining a therapy map, setting out a relationship between applied stimuli regimes and the desired neural response. Device 100 further comprises an electrode array 120 consisting of a three by eight array of electrodes 122, each of which may be selectively used as either the stimulus electrode or sense electrode, or both.

Figure 2:
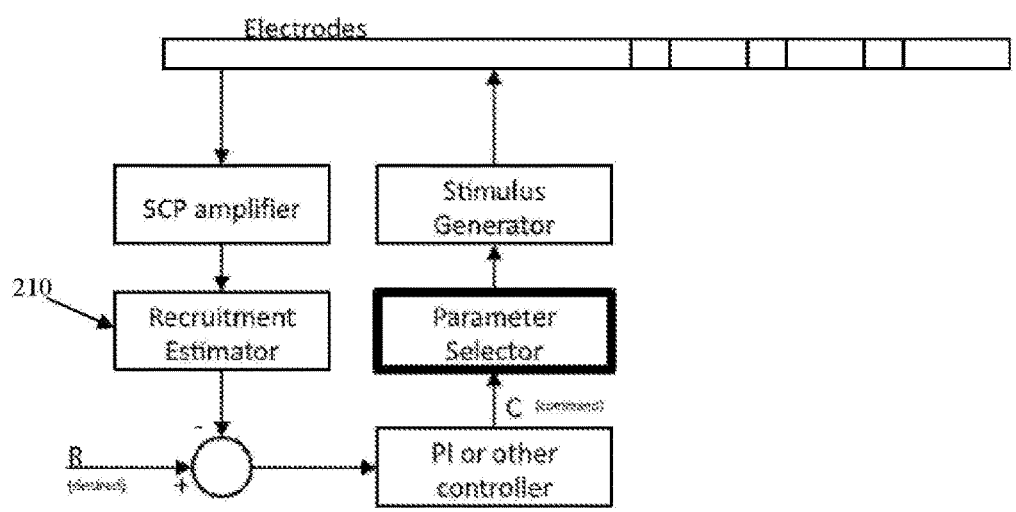
FIG. 2 is a schematic of a feedback controller to effect stimulus control in response to recruitment.

FIG. 2 is a schematic of a feedback controller implemented by the control unit 110, based on recruitment. An important component of such feedback control is a recruitment estimator 210, which is tasked with the difficult operation of in a simple form, detecting whether a neural response is present in a neural measurement output by the spinal cord potential (SCP) amplifier, or in a more complex form determining an amplitude of any such neural response.

The evoked CAP measurements in this embodiment are made by use of the neural response measurement techniques set out in International Patent Publication No. WO2012/155183.

Figure 3A:
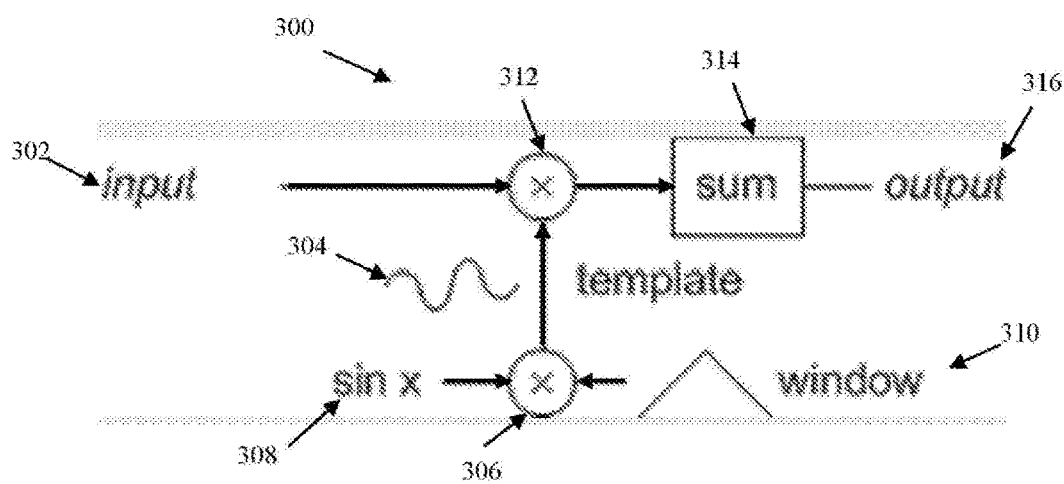
FIG. 3a illustrates a neural response detector in accordance with one embodiment of the invention.
Figure 3B:
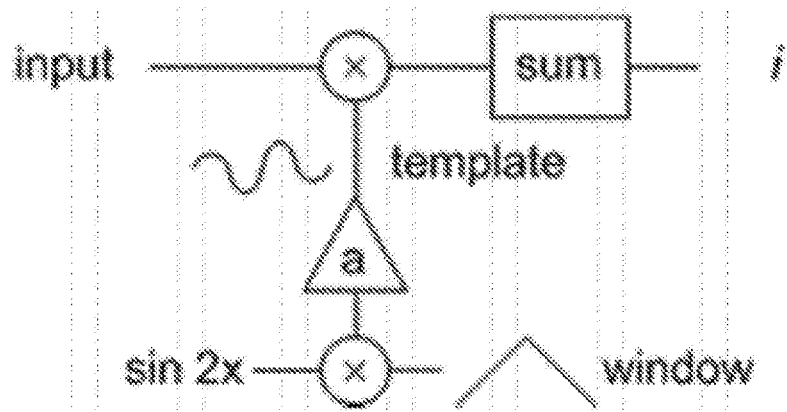

FIG. 3a illustrates a neural response detector 300 in accordance with one embodiment of the invention. A digitised sampled form of the neural measurement obtained by the SCP amplifier is taken as the input 302. A filter template 304 is created at 306 by modulating a sine wave 308 with a Bartlett window 310. In alternative embodiments the template is likely to be predefined in this manner and simply retrieved from a memory or the like within control unit 110. A dot product of a suitable window of the neural measurement 302 and the filter template 304 is calculated at 312, 314, to produce the detector output 316, which is a single value scalar. The detector 300 may be modified as shown in FIG. 3b by the addition of a gain term "a" for example to allow the correlator to produce approximately the same result as a peak-to-peak ECAP detector for comparison.

Figure 4:
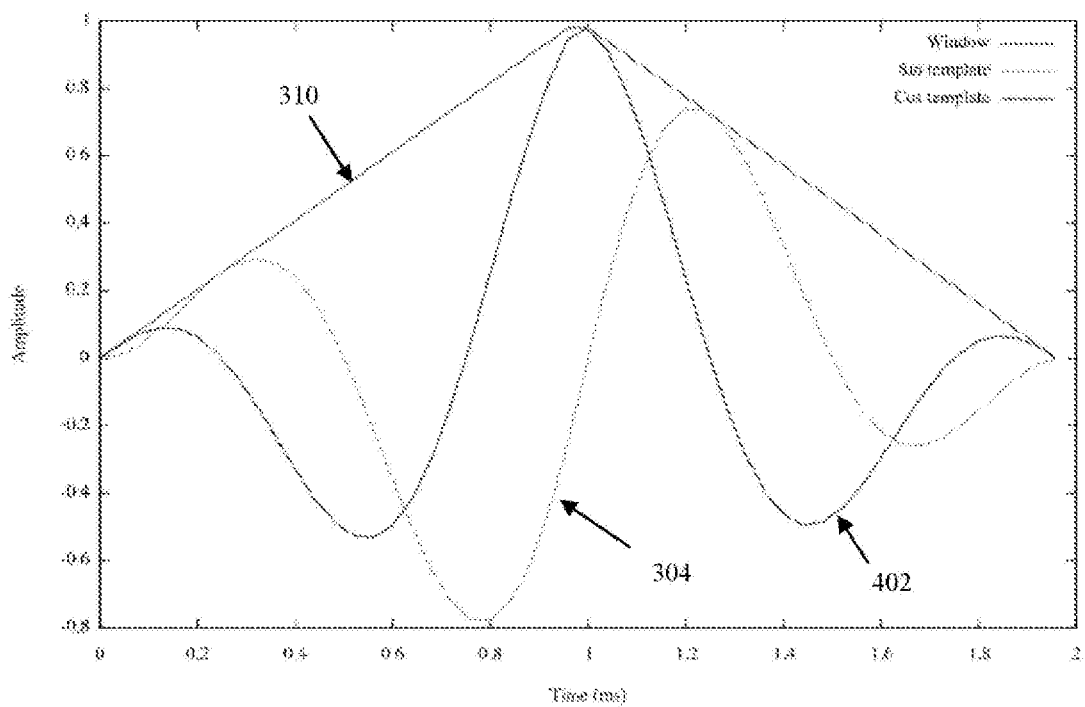
FIG. 4 illustrates the amplitude profile of the filter template used in the detector of FIG. 3; and a cosine filter template, and the Bartlett window.

FIG. 4 illustrates the amplitude profile of the filter template 304 used in the detector 300 of FIG. 3. FIG. 4 further illustrates the Bartlett window 310 used to amplitude modulate the sine wave 308. To assist in the following discussion, FIG. 4 also shows an additional filter template 402, comprising a cosine wave amplitude modulated by the Bartlett window 310. It is noted on the x-axis of FIG. 4 that the filter templates 304 and 402 each comprise a sufficient number of points such that at the sampling rate used the filter templates each cover a time period of almost 2 ms, which is four-thirds of the duration of an expected neural response in this embodiment.

Figure 5A:
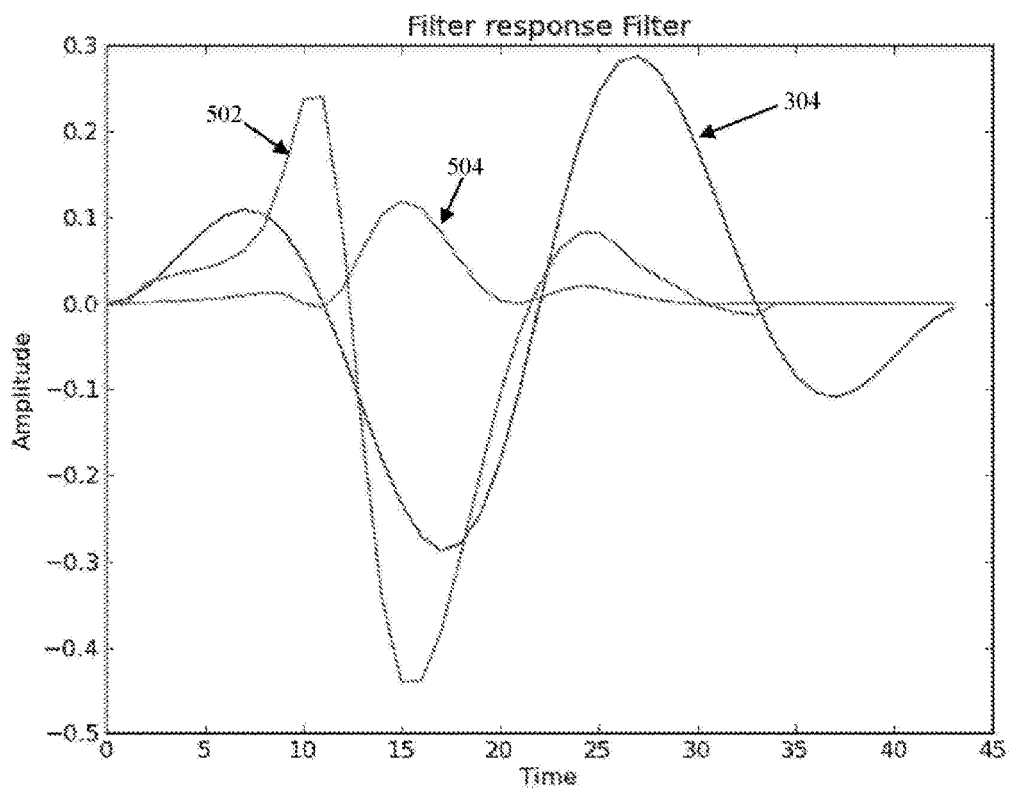
FIG. 5a illustrates the ability of the filter template to pass an evoked response.
Figure 5B:
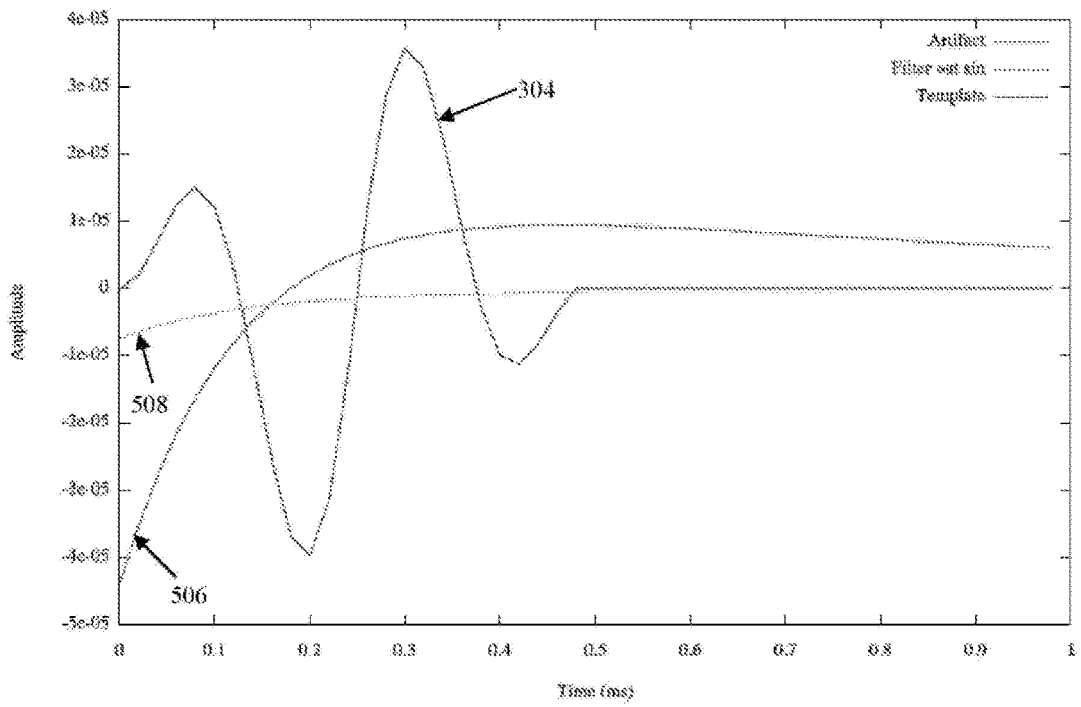
FIG. 5b illustrates the ability of the filter template to block artifact.

FIG. 5a illustrates an evoked response 502 in the absence of artifact, the four-lobe filter template 304, and the sliding dot product or cross correlation thereof, 504. Again, it is noted that the response 502 comprises three lobes, whereas the filter template 304 comprises four lobes and is four-thirds the expected length of the response 502. As can be seen in the sliding dot product 504, the evoked response 502 is substantially passed to the output of the detector 300 by the filter template 304. In contrast FIG. 5b illustrates the correlation 508 of the four lobe filter template 304 with pure artifact 506, illustrating that artifact is substantially blocked or heavily attenuated by the filter template 304 and thus not passed to the output of the detector 300. In this embodiment, the performance of the four-lobe filter template 304 at passing an expected neural response is within 2 dB of that of a matched filter, but with significantly improved artifact rejection.

It is noted that when sampling at 10 kHz, for example, 20 samples will be obtained in a 2 ms window, so that to determine the entire cross correlation will require 400 multiply/add operations. Accordingly, rather than calculating the entire cross-correlation between a measured neural response and the filter template, the present embodiment further provides for calculation of only a single point of the correlation as the output 316 of detector 300, as a single point requires only 20 samples when sampling a 2 ms window at 10 kHz. Noting that the arrival time of the neural response, or its position within the neural measurement 302, is not known a priori, it is necessary to determine an optimal time delay or offset between the neural measurement and the template filter, at which the single point of the correlation should then be calculated. The aim is to calculate the single point at the peak of the curve 504, and no other. To this end, the present embodiment efficiently determines the optimal time delay, by noting the following.

The DFT is defined by:

$$X_k = \sum_{n=0}^{N-1} x_n \cdot e^{-i2\pi kn/N} \qquad (1)$$

In equation (1), and in the rest of this document, frequency-domain signals are represented by capital letters, and time-domain signals using lower-case. When using the DFT for spectral analysis, it is usual to multiply the data by a window W(n) so this becomes:

$$X'_k = \sum_{n=0}^{N-1} x_n \cdot W(n) \cdot e^{-i2\pi kn/N} \qquad (2)$$

This can be expressed in traditional magnitude and phase terms where the magnitude of the windowed DFT term is $$|X'_k| = \sqrt{Re(X'_k)^2 + Im(X'_k)^2} \qquad (3)$$

and the phase of the windowed DFT term is $$\Phi'_k = \tan^{-1}\left(\frac{Re(V'_k)}{Im(V'_k)}\right) \qquad (4)$$

The hardware 600 used to compute one term of $X'_k$ is illustrated in FIG. 6. Notably, the sine template 304 and cosine template 402 shown in FIG. 4 are used in the circuit 600. Comparing this arrangement to the previous equation, for which the third term is:

$$X'_2 = \sum_{n=0}^{N-1} x_n \cdot W(n) \cdot e^{-i4\pi n/N}, \qquad (5)$$

it is noted that detector 300 using the filter template 304 (FIG. 3) computes the imaginary part of the third term of the windowed DFT. Thus, references to the output of the detector 300 are to be understood as being the imaginary part of the third term of the windowed DFT, and this is important to an understanding of the following further refinements of the invention.

This also provides insight into what happens as the time delay is adjusted during a clinical fitting procedure, as shown in FIG. 7. While FIG. 7b shows a triangular window and a single lobed response, this is for simplicity of representation and is intended to represent the four lobed filter template 304 and the three lobed response 502, respectively. Exploring different time delay adjustments by sliding the offset or delay in the time domain (FIG. 7b), rotates the coordinate system of the measurement (FIG. 7a). When the evoked response phase aligns with the imaginary axis of FIG. 7a, the output of the detector 300 is at its maximum. This also presents a computationally efficient solution to the problem when at this phase; when the correlator output is maximum, the real part of the spectral component is zero, so its calculation can be avoided as depicted in FIG. 3, saving processor cycles. The output of the detector 300 is the projection of the (complex) evoked response onto the imaginary axis.

When considering the entire cross correlation as the evoked response slides across the window (FIG. 7b), the evoked response vector in FIG. 7a rotates a full 360 degrees around the origin at least twice, and thus changes relatively quickly. However as shown at the bottom of FIG. 7b, the amplitude of the convolution of the evoked response and the window changes relatively slowly. Accordingly, the present embodiment recognises that a swift technique to align the evoked response with the imaginary axis and thus find the peak in the correlator output is to:

1. Roughly align the window and the signal S(t);
2. Calculate the imaginary (sin) and real (cosine) terms:

$I = S(t) \cdot W(t) \cdot \sin(1\ KHz \cdot 2\pi \cdot t)$, and      a.

$Q = S(t) \cdot W(t) \cdot \cos(1\ KHz \cdot 2\pi \cdot t)$;      b.

3. Find the angle to the y-axis using atan(Q/I);
4. As the template has fixed known frequency, calculate the time shift needed to set the sin term to its maximum;
5. Calculate the imaginary (sin) and real (cosine) terms for the new delay. The cosine term should be much smaller than the sin term confirming that the method worked.

Such embodiments may be particularly advantageous as compared to a clinical process requiring exploration of the varying delays in order to find a peak.

The present embodiment further incorporates the third and fourth aspects of the invention, and recognises that the artifact 506 can be well modelled as being a sum of two exponentials, of differing time constant. Each exponential component has a voltage and a time value, leading to $$a(t) = v_1 \exp\left(\frac{-t}{\tau_1}\right) + v_2 \exp\left(\frac{-t}{\tau_2}\right) \qquad (6)$$

where $v_1$ and $\tau_1$ are constants for each component.

If $$e(t) = v \exp(-t/\tau) \qquad (7)$$

then we can consider its windowed DFT $E'_k$, for which each term will have a magnitude and phase, and the term $E'_2$ can be calculated with the complex correlator 600 of FIG. 6.

If we take some signal $e^{-t/\tau}$ and shift the point in the signal at which the correlation is performed by some arbitrary time T, since $$e^{-(t+T)/\tau} = e^{-t/\tau} e^{-T/\tau}$$

$$e^{-(t+T)/\tau} = e \cdot e^{-t/\tau} \qquad (8)$$

where e is some constant.

Thus, the phase of the DFT terms of a single exponential depend on the time constant of the exponential, as shown in FIG. 8 for the filter template 304. However, the present embodiment recognises that the phase of each DFT term is unchanged by time delay.

FIG. 9 illustrates the filter output vector components arising from artifact only, when modelled as two exponentials. At a first time, shown in FIG. 9a, $A_2$ and $B_2$ are the two artifact phase vectors. These can be added using vector addition to produce the total artifact 902. The detector 300 will thus produce an output 904 which is the imaginary part of this vector, the projection of 902 onto the y-axis. As time passes, the lengths of the two vectors reduce exponentially, but at different rates as the time constants are different, B2 decaying rapidly and A2 decaying slowly. However, the phases remain unchanged as per equation (8), resulting in the situation shown in FIG. 9b. The total artifact vector is now 912, which due to the different relative contributions from each exponential component is of slightly changed phase to 902. The detector 300 will thus produce an output 914.

FIGS. 10a and 10b illustrate, at respective times, the detector output vector components arising from artifact modelled as two exponentials and from an evoked response. At a first time t, shown in FIG. 10a, $V_1$ and $V_2$ are the two artifact phase vectors, and CAP is the evoked response vector. These can be added using vector addition to produce the total artifact 1002. The detector 300 will thus produce an output 1004 which is the imaginary part of this vector, the projection of 1002 onto the y-axis. At a later time t+dt, the lengths of the two artifact vectors have reduced exponentially, at different rates as the time constants are different, with $V_2$ decaying rapidly and $V_1$ decaying slowly. However, the phases remain unchanged as per equation (8), as shown in FIG. 10b. In contrast, the amplitude of the evoked response vector CAP changes relatively slowly as discussed in relation to FIG. 7b, but undergoes a change in phase as discussed in relation to FIG. 7a. Thus, as shown in FIG. 10b, the CAP vector rotates without undergoing a significant amplitude change. Thus, at one moment (FIG. 10a) the CAP vector can be orthogonal to $V_2$, and at a later time (FIG. 10b) can be aligned with $V_2$.

When modelling the artifact as a sum of two exponential terms, it has been determined from measurements of actual artifact that the time constant $\tau_1$ of the first (slow) exponential term is typically in the range 300 ms to 30 ms, more typically 500 μs to 3 ms and most commonly about 1 ms, and that the time constant $\tau_2$ of the second (fast) exponential term is typically in the range 60-500 μs, more typically 100-300 μs, and most commonly about 150 μs.

Figure 11A:
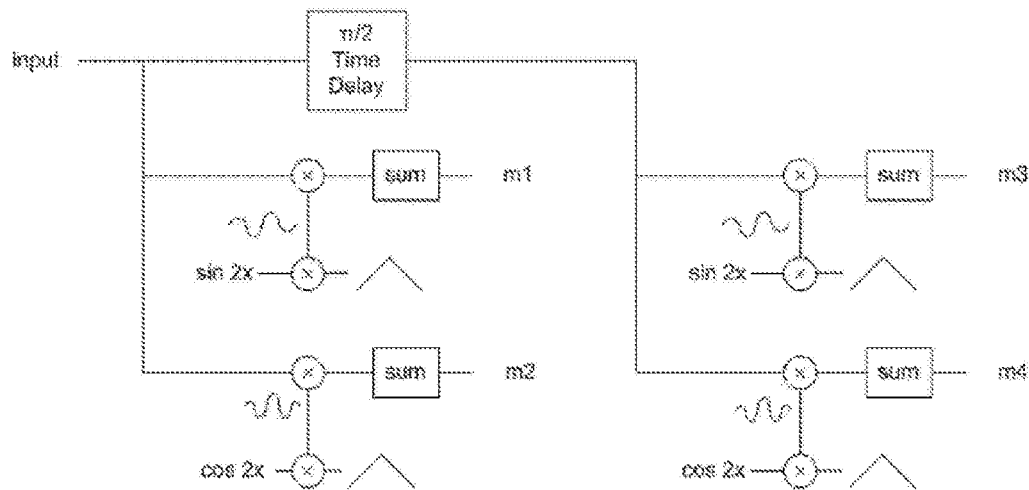
FIGS. 11a and 11b illustrate a four point measurement technique for measuring a CAP.

The method of this embodiment, utilising the third and fourth aspects of the invention, relies on making two complex measurements of the evoked response, at points in time separated by one quarter of a cycle, as shown in FIG. 11a. The timing of the measurements is optimised in the manner described above in relation to FIG. 7, so that the first measurement (m1 and m2) has a purely imaginary evoked response contribution (i.e. the evoked response aligns with the sin correlator 304), and the second measurement (m3 and m4) is purely real (i.e. aligns with the cosine 402). This leads to four measurements, m1 to m4. There are four unknowns—the magnitude of the artifact, the magnitude of the evoked response, the phase of the artifact and the time constant of the fast exponential. The slow exponential component of the artifact is well rejected by the filter template 304 and thus can be omitted. It is known that the artifact contribution to the sin and cos correlators has a fixed ratio. Using simple algebra the unknowns can be eliminated. Therefore any CAP present in the neural measurement can be calculated as being:

$$CAP = m_4 - k \cdot m_2 \quad (9)$$

$$\text{Where } k = \frac{m_4 - m_1 \pm \sqrt{(m4-m1)^2 + 4 \cdot m2 \cdot m3}}{2 \cdot m2} \quad (10)$$

Figure 11B:
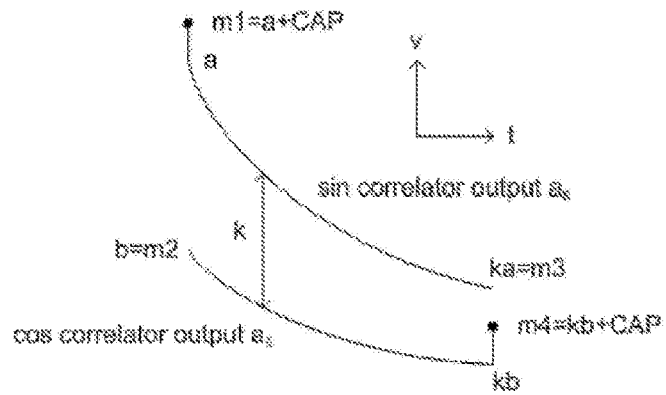

FIG. 11b illustrates the locations of these four measurements m1 to m4 on the real and imaginary detector outputs.

Knowing k also allows the evaluation of $\tau$, and of the fast artifact exponential:

$$\tau = \frac{-T}{\ln(k)} \quad (11)$$

To find the voltage of the fast exponential term for the artifact, one can further calculate the DFT of the exponential which is what would be expected from the detectors for an exponential input of that time constant, normalized to 1.0:

$$X_2' = \sum_{n=0}^{N-1} e^{\frac{-t}{\tau}} \cdot W(n) \cdot e^{-i4\pi n/N} \quad (12)$$

Then, an estimation of the fast artifact term is:

$$A(t) = \frac{e^{-t/\tau}}{X_2'} \quad (13)$$

Figure 12:
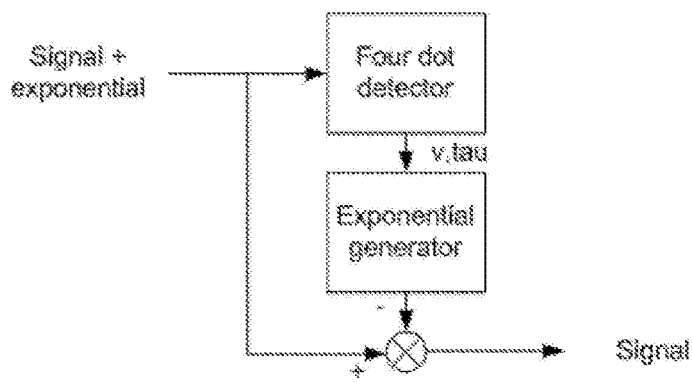
FIG. 12 illustrates exponential estimation and subtraction.

Having calculated the above, it is possible to improve the SAR of the signal by subtracting the estimated exponential, as shown in FIG. 12.

A difficulty in implementing this algorithm with measured data is that it measures two signals at once, namely the evoked response and the fast exponential, and each forms a noise source for the other. Usually, the phase of the evoked response is not known exactly, and this introduces errors into FIG. 11b. When the evoked response is larger than the exponential, and the phase of the evoked response is not known, the exponential estimation algorithm does not always find a solution, so the present embodiment further provides a second estimation method for these circumstances. This further estimation method recognises that the above algorithms can be extended by adding an additional correlation, to allow the phase of the evoked response to be calculated instead of being used as an input.

Figure 13:
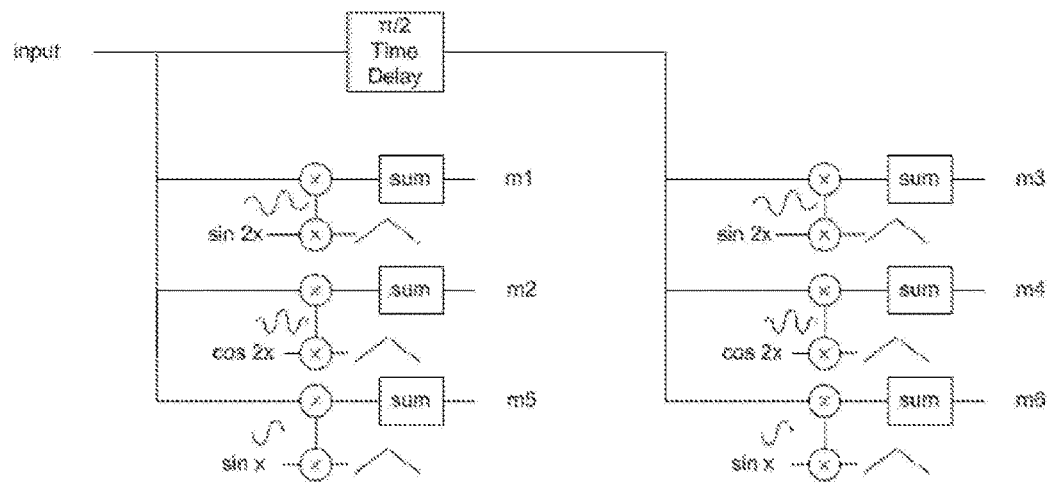
FIG. 13 illustrates a system for 6 point detection for when relative phase between evoked response and sampling window is unknown.

When the relative phase (θ) of the evoked response to the sampling window is unknown, the proposal of FIG. 11 has 5 unknowns and 4 measurements, so the unknowns cannot be found. By adding two more DFT points this can be overcome, as shown in FIG. 13. These additional points (m5 and m6) are evaluated at a frequency equal to half the fundamental of the evoked response—to which the evoked response is orthogonal. Therefore these two additional points allow k to be evaluated:

$$k = \frac{m6}{m5} \quad (14)$$

In turn, the five terms a, b, k, θ and c can be found. For some phase θ between the measurement window and the evoked response:

m1=a+c sin θ m2=b+c cos θ m3=ak+c cos θ m4=bk+c sin θ  (15)

so:

$$a = \frac{(m1 - m4) + k(m2 - m3)}{1 - k^2} \quad (16)$$

$$b = m2 - m3 + ak \quad (17)$$

$$c = \sqrt{(m1 - a)^2 + (m2 - b)^2} \quad (18)$$

$$\theta = \sin^{-1}\left(\frac{m1 - a}{c}\right) \quad (19)$$

The phase will change slowly, so once θ is known, it is possible to adjust the delay of the sampling window, and then revert to the four point algorithm of FIG. 11.

When considering implementation of the six point technique of FIG. 13, it is noted that in some embodiments an FFT will compute this faster than a DFT, especially if the FFT is factored to use the smallest number of multiply operations. A good choice of DFT length might be 16, factored as $(F_2 \circ F_2) \circ (F_2 \circ F_2)$. For this factorization the twiddle factors between the $F_2$ operations are trivial, and so the only complex multiply required is in the middle.

Figure 14:
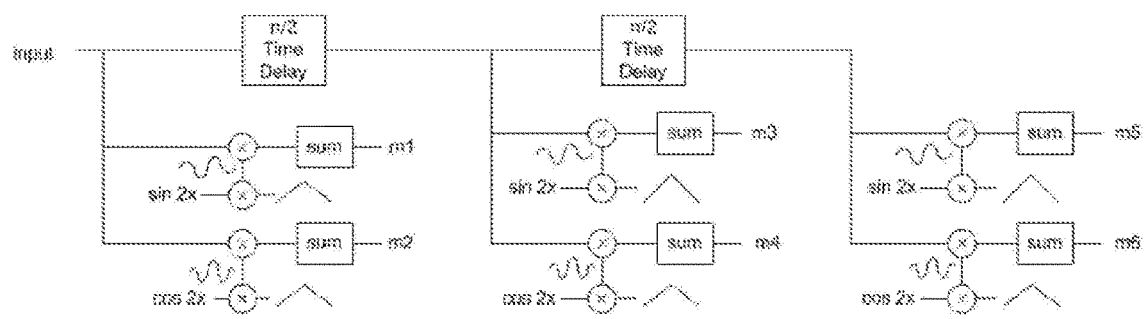
FIG. 14 illustrates an alternative embodiment for 6-point detection.

FIG. 14 illustrates an alternative embodiment utilising six measurement points.

It is further noted that running the calculation after the evoked response is finished allows the slow exponential to be measured.

The evoked response in the spine (having three phases) takes approximately 1 ms. In embodiments employing a sample rate of 30 KHz or a simple interval of 33 μs, the evoked response will take around 30 samples. Consequently in such embodiments the filter template having four phases will comprise approximately 40 tap values, or data points. In alternative embodiments, using an alternative sampling rate or measuring a faster or slower CAP, the length of the filter may comprise correspondingly greater or fewer filter taps.

While the preceding embodiments have been described in relation to a filter template which comprises four half cycles, alternative embodiments of the present invention may nevertheless usefully employ a filter template comprising greater or fewer lobes. The present invention thus recognises that the ideal number if lobes is four. This is in contrast to a two lobe filter, which will have equal first and second lobes and will thus put more emphasis on the early parts of the signal where the signal-to-artifact is worse. Further, a filter with an odd number of lobes does not tend to have good artifact rejection properties. Moreover, if one were to use a six-lobe filter, or higher even-number lobed filter, the window becomes too wide relative to the 3-lobed neural response, and at least half the correlation time would just be looking at noise. Since most of the problematic artifact is in the first two lobes, a 6 lobe filter will tend not to provide better artifact rejection than the four-lobe filter. Four lobes thus provides the optimal trade-off between rejection of artifact and noise gain.

Figure 15A:
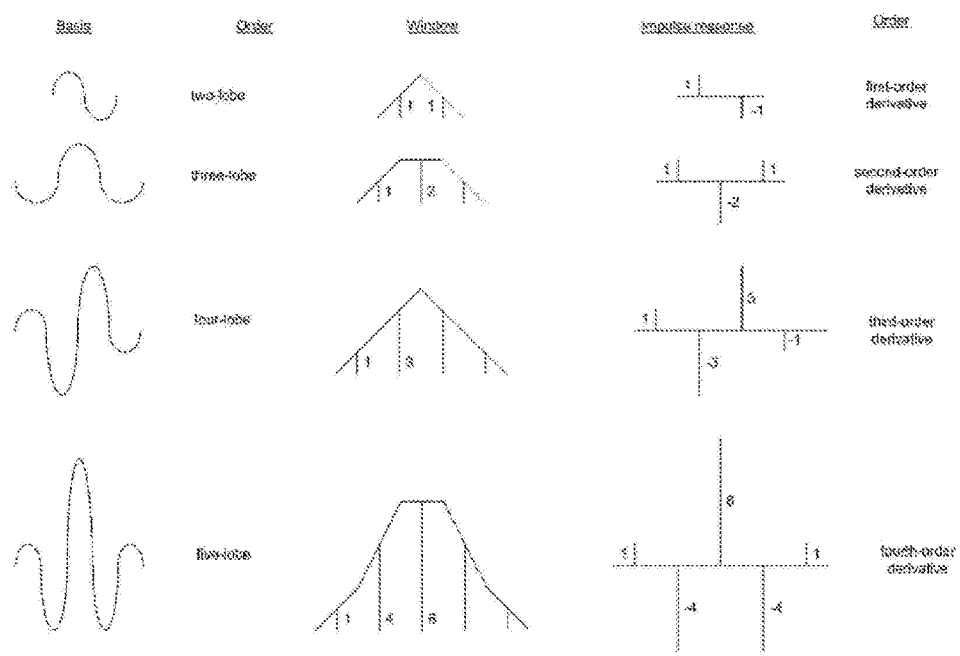
FIGS. 15a and 15b illustrates generation of filter templates having three, four and five lobes, respectively.
Figure 15B:
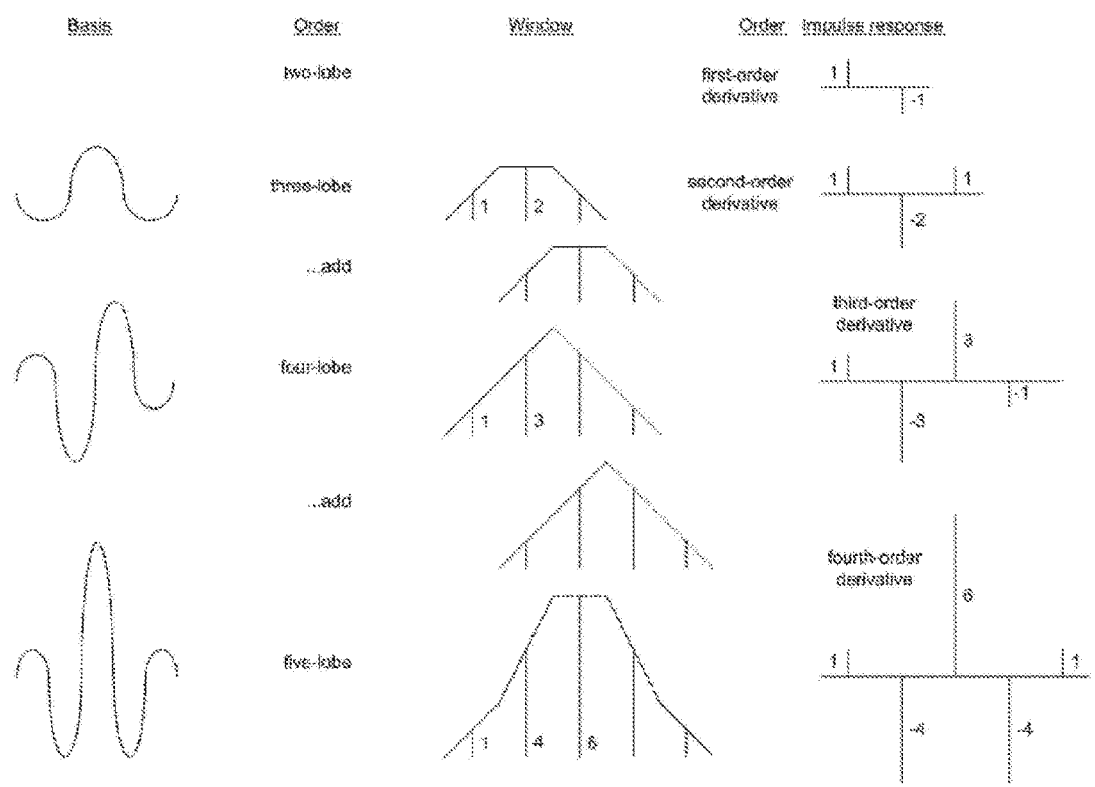

Nevertheless, alternative embodiments of the present invention may usefully employ a filter template comprising greater or fewer lobes. We now describe the mathematical properties of templates of other embodiments of the invention. The term "template" is used to refer to a filter used via correlation to detect an ECAP. A template may be comprised of one or more wavelets or basis functions, or may be derived by some other method, and is configured to preferentially pass an ECAP but preferentially block or be orthogonal to artifact. FIG. 15a illustrates sinusoidal binomial vectors in accordance with further embodiments of the invention. FIG. 15b shows the generation of three-lobe, four-lobe and five-lobe templates. A notable property of the SBT is that its basis functions of the same length are orthogonal. It is to be appreciated that the method used to generate the templates of FIG. 15 up to five-lobes can be extended to a greater number of lobes. It is further noted that the window is not triangular for three or five lobed filter templates, but has a flat central portion in both cases, and in the case of five lobes the window having a piecewise linear rise and fall. Thus, the three lobed filter template window proposed by the present embodiments is not triangular but is a flat topped window, which has been found to significantly improve artifact rejection as compared to a triangular window of a three lobed filter template.

That is, an important property of the sinusoidal binomial transform (SBT) is its ability to reject polynomial signals. If an SBT template of order n is used, it will reject all the terms of the Taylor series up to order n.

Figure 16A:
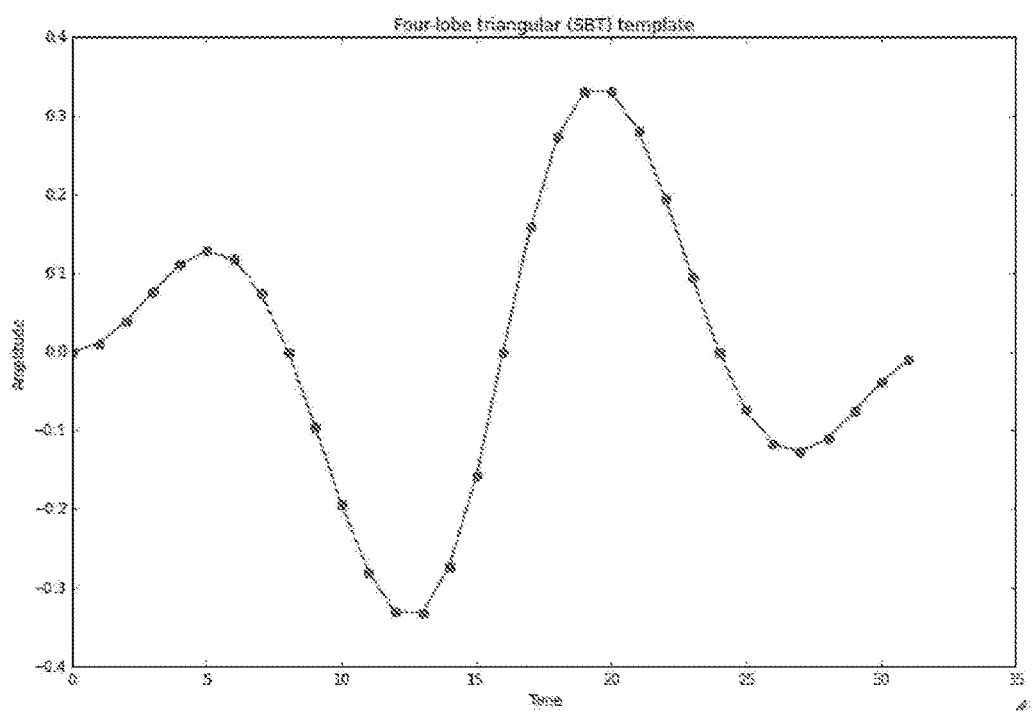
FIGS. 16a and 16b respectively illustrate four and three lobed filter template point values, derived from the approach of FIG. 15.
Figure 16B:
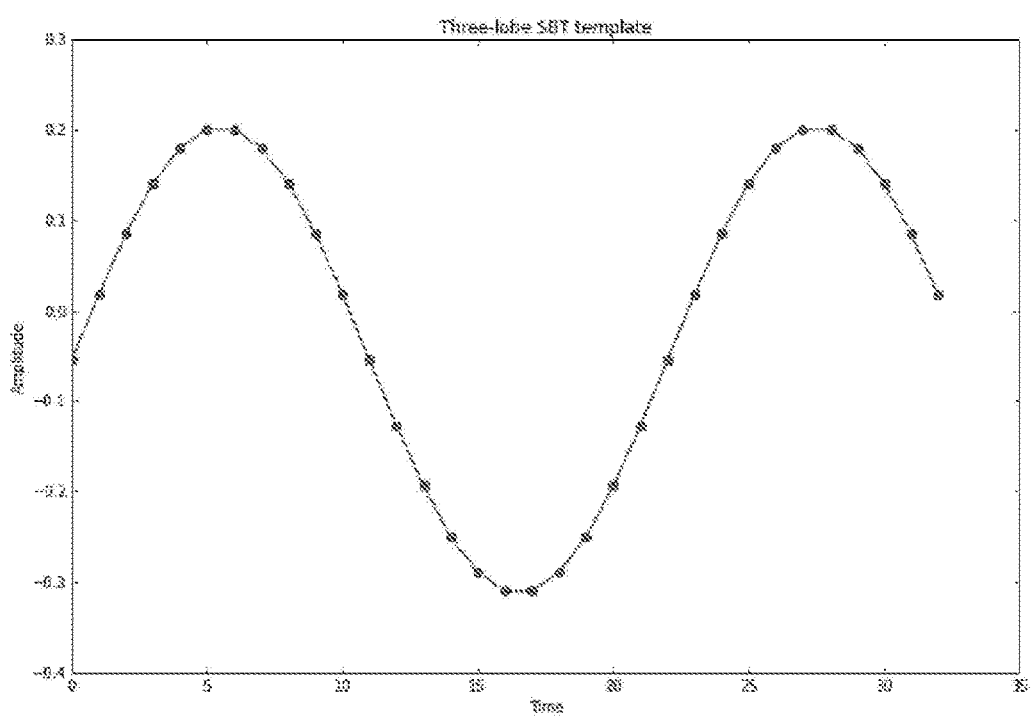

FIG. 16a illustrates the point values of a four lobed, 32 point filter template generated in accordance with the teachings of FIG. 15. FIG. 16b illustrates the point values of a three lobed, 33 point filter template generated in accordance with the teachings of FIG. 15 and in particular having a flat topped window.

It is further to be appreciated that cosine templates of 3, 5 or more lobes can be similarly generated, noting the FIG. 4 example for a four half cycles cosine template 402.

The preceding embodiments further describe a filter template built using a triangular window. The triangular window is superior to the Bartlett, Hanning, rectangular and the Kaiser-Bessel for a variety of beta values. The performance of the four-lobe triangular template can be within 2 dB of a matched filter for optimised offset. Nevertheless, alternative embodiments may utilise windows other than the triangular window to useful effect, and such embodiments are thus within the scope of the present invention.

Moreover, while the described embodiments use a single term of the SBT for response detection, the present invention further recognises that there are possible extensions to this method. Therefore, some embodiments of the invention may use multiple identical templates, but shifted in time. Even though these are not orthogonal, a successive approximation method creating a compound template may provide better approximation. Additionally or alternatively, some embodiments may use templates that are a sum of templates of different frequencies, templates of different offset and/or templates of different numbers of lobes.

A benefit of some embodiments of the present invention is that in some embodiments the detector produces an output based on a single neural measurement, without requiring multiple neural measurements to produce a detector output. Such embodiments may thus provide a swift response time of a feedback control loop utilising the detector output.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for processing a neural measurement obtained in the presence of artifact, in order to detect whether a neural response is present in the neural measurement, the method comprising:

obtaining a neural measurement from one or more sense electrodes, the neural measurement being obtained in the presence of artifact;

correlating the neural measurement against a filter template, the filter template comprising at least three half cycles of an alternating waveform, amplitude modulated by a window; and determining from an output of the correlating whether a neural response is present in the neural measurement.

2. The method of claim 1 wherein the window comprises a triangular window.

3. The method of claim 2 wherein the triangular window is a standard triangular window of length L comprising coefficients w(n) as follows:

For $L$ odd:

$$w(n) = 2n/(L+1) \text{ for } 1 \leq n \leq (L+1)/2$$
$$= 2 - 2n(L+1) \text{ for } (L+1)/2 + 1 \leq n \leq L$$

For $L$ even:

$$w(n) = (2n-1)/L \text{ for } 1 \leq n \leq L/2$$
$$= 2 - (2n-1)/L \text{ for } L/2 + 1 \leq n \leq L.$$

4. The method of claim 2 wherein the triangular window is a Bartlett window in which samples 1 and L are zero.

5. The method of claim 1 wherein the window comprises one of a Hanning window, a rectangular window or a Kaiser-Bessel window.

6. The method of claim 1 wherein the window comprises one or more basis functions derived from a sinusoidal binomial transform.

7. The method of claim 1 wherein the filter template comprises four half-cycles of an alternating waveform.

8. The method of claim 1 wherein the filter template comprises half cycles of a sine wave, modified by being amplitude modulated by the window.

9. The method of claim 1 wherein the filter template comprises half cycles of a cosine wave, modified by being amplitude modulated by the window.

10. The method of claim 1 wherein only a single point of the correlation is calculated.

11. The method of claim 10 wherein the single point of the correlation is calculated at a predefined optimal time delay.

12. The method of claim 11, further comprising determining the optimum time delay when a signal to artifact ratio is greater than one, at which a first or single point of the cross-correlation between the neural measurement and the filter template should be produced, by:

at an approximate time delay between the neural response and the filter template, computing real and imaginary parts of the fundamental frequency of the DFT of the neural measurement;

calculating a phase defined by the real and imaginary parts;

relative to a fundamental frequency of the template, calculating the time adjustment needed to change the calculated phase to $\pi/2$; and defining the optimum time delay as being the sum of the approximate time delay and the time adjustment.

13. The method of claim 11, wherein the optimum time delay is recalculated prior to every attempted detection of a neural response.

14. The method of claim 11, wherein the optimum time delay is recalculated in response to a detected change in the user's posture.

15. An implantable device for processing a neural measurement obtained in the presence of artifact, in order to detect whether a neural response is present in the neural measurement, the device comprising:

measurement circuitry for obtaining a neural measurement from one or more sense electrodes, in the presence of artifact; and a processor configured to correlate the neural measurement against a filter template, the filter template comprising at least three half cycles of an alternating waveform, amplitude modulated by a window; and the processor further configured to determine from an output of the correlating whether a neural response is present in the neural measurement.

* * * * *

UNITED STATES PATENT AND TRADEMARK OFFICE
CERTIFICATE OF CORRECTION

PATENT NO. : 10,426,409 B2
APPLICATION NO. : 15/037038
DATED : October 1, 2019
INVENTOR(S) : Peter Scott Vallack Single Page 1 of 1

It is certified that error appears in the above-identified patent and that said Letters Patent is hereby corrected as shown below:

In the Specification

The equation at Column 3, Line 49 to Line 54:
"For L odd:
$w(n) = 2n / (L+1)$ for $1 \leq n \leq (L+1) / 2$
$\phantom{w(n)} = 2 - 2n(L+1)$ for $(L+1) / 2 + 1 \leq n \leq L$"

Should read:
-- For L odd:
$w(n) = 2n / (L+1)$ for $1 \leq n \leq (L+1) / 2$
$\phantom{w(n)} = 2 - 2n / (L+1)$ for $(L+1) / 2 + 1 \leq n \leq L$ --.

In the Claims

The equation at Column 15, Line 17 to Line 23 in Claim 3:
"For L odd:
$w(n) = 2n / (L+1)$ for $1 \leq n \leq (L+1) / 2$
$\phantom{w(n)} = 2 - 2n(L+1)$ for $(L+1) / 2 + 1 \leq n \leq L$"

Should read:
-- For L odd:
$w(n) = 2n / (L+1)$ for $1 \leq n \leq (L+1) / 2$
$\phantom{w(n)} = 2 - 2n / (L+1)$ for $(L+1) / 2 + 1 \leq n \leq L$ --.

Signed and Sealed this
Eleventh Day of February, 2020

Andrei Iancu
*Director of the United States Patent and Trademark Office*